US012773444B2

(12) United States Patent
Trzonkowski et al.

(10) Patent No.: US 12,773,444 B2
(45) **Date of Patent: *Oct. 27, 2026**

(54) THERAPEUTIC VACCINE FOR TREATMENT OF DIABETES TYPE 1 IN CHILDREN, APPLICATION OF THE CELL SORTER AND THE METHOD OF MULTIPLYING TREG CELLS TO PRODUCE THERAPEUTIC VACCINE FOR TREATMENT OF DIABETES TYPE 1

(71) Applicant: Gdanski Uniwersytet Medyczny, Gdansk (PL)

(72) Inventors: Piotr Trzonkowski, Sopot (PL); Malgorzata Mysliwiec, Gdansk (PL); Natalia Marek-Trzonkowska, Gdansk (PL)

(73) Assignee: Gdanski Uniwersytet Medyczny, Gdansk (PL)

( * ) Notice: Subject to any disclaimer, the term of this patent is extended or adjusted under 35 U.S.C. 154(b) by 0 days.

This patent is subject to a terminal disclaimer.

(21) Appl. No.: 18/588,535

(22) Filed: Feb. 27, 2024

(65) Prior Publication Data

US 2024/0197848 A1 Jun. 20, 2024

Related U.S. Application Data

(60) Division of application No. 15/852,227, filed on Dec. 22, 2017, now Pat. No. 11,944,672, which is a continuation of application No. 14/405,906, filed as application No. PCT/PL2013/000072 on Jun. 4, 2013, now abandoned.

(30) Foreign Application Priority Data

Jun. 6, 2012 (PL) .................................... P.399447

(51) Int. Cl.

| | |
|---|---|
| ***A61K 39/00*** | (2006.01) |
| ***A61K 35/26*** | (2015.01) |
| ***A61K 40/11*** | (2025.01) |
| ***A61K 40/22*** | (2025.01) |
| ***A61K 40/41*** | (2025.01) |
| ***C12N 5/0783*** | (2010.01) |
| ***C12N 13/00*** | (2006.01) |

(52) U.S. Cl.

CPC .......... *A61K 39/0008* (2013.01); *A61K 35/26* (2013.01); *A61K 40/11* (2025.01); *A61K 40/22* (2025.01); *A61K 40/416* (2025.01); *C12N 5/0637* (2013.01); *C12N 13/00* (2013.01); *A61K 2039/55* (2013.01); *A61K 2239/31* (2023.05); *A61K 2239/38* (2023.05); *C12N 2501/2302* (2013.01); *C12N 2502/11* (2013.01)

(58) Field of Classification Search

None

See application file for complete search history.

(56) References Cited

U.S. PATENT DOCUMENTS

| | | | | |
|---|---|---|---|---|
| 2009/0142308 | A1 | 6/2009 | Orban | |
| 2009/0208471 | A1 | 8/2009 | Yun | |
| 2009/0232774 | A1 | 9/2009 | Reisner | |
| 2011/0300119 | A1* | 12/2011 | Tran ..................... | A61K 40/416 435/375 |
| 2013/0157363 | A1 | 6/2013 | Kim | |

FOREIGN PATENT DOCUMENTS

| | | | |
|---|---|---|---|
| WO | 2004/110373 | A2 | 12/2004 |
| WO | 2012/001099 | A1 | 1/2012 |
| WO | 2012/001100 | A1 | 1/2012 |

OTHER PUBLICATIONS

Neal, 2017, J. Immunol. Res. Ther. vol. 2: 68-79.*

Golab et al., Impact of culture medium on CD4(+) CD25(high) CD 127(lo/neg) Treg expansion for the purpose of clinical application, International Immunopharmacology, 2013, 16(3), 358-363.

Trzonkpwski et al., Differences in kinetics of donor lymphoid cells in response to G-CSF administration may affect the incidence and severity of acute GvHD in respective HLA-identical sibling recipients, Med Ocol. 2004, 21(1), 81-94.

Green et al., CD4+CD25+ T regulatory cells control anti-islet CD8+ T cells through TGF-beta-TGF-beta receptor interactions in type 1 diabetes, PNAS, 2003, 100(19), 8, 10878-10883.

Green et al., Pancreatic lymph node-derived CD4(+)CD25(+) Treg cells: highly potent regulators of diabetes that require Trance-Rank signals, Immunity, 2002, 16(2), 183-191.

International Search Report for International Application No. PCT/PL2013/000072 with a mailing date of Oct. 22, 2013.

Liu, et al., CD 127 expression inversely correlates with FoxP3 and suppressive function of human CD4(+) t reg cells, Journal of Experimental Medicine, 2006, 203(7), 1701-1711.

Marek et al., Coating human pancreatic islets with CD4(+)CD25(high)CD127(−) regulatory T cells as a novel approach for the local immunoprotection. Ann Surg. 2011, 254(3), 512-8; discussion 518-9.

Marek et al., The Time is Crucial for Ex Vivo Expansion of T Regulatory Cells for Therapy, Cell Transplantation, 2011, 20, 1747-1758.

Marek-Trzonkowska et al., Administration of CD4+CD25highCD127— regulatory T cells preserves β-cell function in type 1 diabetes in children, Diabetes Care, 2012, 35(9), 1817-1820.

Ryba et al., Anti-TNF rescue CD4+Foxp3+ regulatory T cells in patients with type 1 diabetes from effects mediated by TNF. Cytokine. 2011, 55(3), 353-61.

(Continued)

*Primary Examiner* — Amy E Juedes

(74) *Attorney, Agent, or Firm* — Arrigo, Lee, Guttman & Mouta-Bellum LLP

(57) ABSTRACT

The gist of the invention consists in the therapeutic vaccine for treatment of diabetes type 1 in children, which contains Treg cells CD3(+)CD4(+)CD25(high)CD127(−). Claimed too is the cell sorter used to produce the vaccine and the method of multiplying Treg cells in vitro.

4 Claims, 2 Drawing Sheets

(56) References Cited

OTHER PUBLICATIONS

Figure 1:
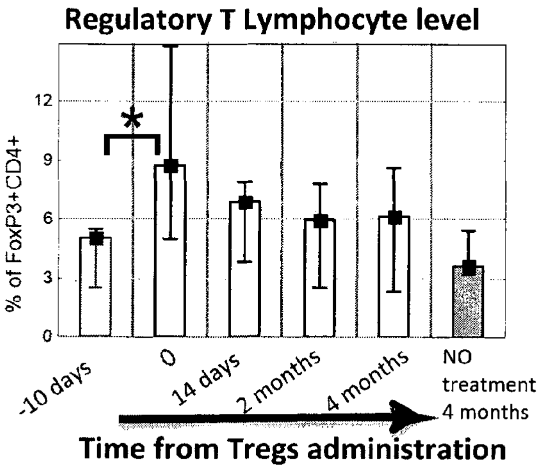

Saloman, B. et al., B7/CD28 costimulation is essential for the homeostasis of the CD4+CD25+ immunoregulatory T cells that control autoimmune diabetes, Immunity, 2000, 12(4), 431-440.
Shevach, Regulatory T cells in autoimmunity, Annual Review of Immunology, 2000, 18(1), 423-449.
Simonetta et al., Increased CD127 expression on activated FOXP3+ CD4+ regulatory t cells, European Journal of Immunology, 2010, 40(9), 2528-2538.
Trzonkowski et al., CD4+CD25+ T regulatory cells inhibit cytotoxic activity of T CDS+ and NK lymphocytes in the direct cell-to-cell interaction, Clin Immunol, 2004, 112(3), 258-67.
Trzonkowski et al., CD4+CD25+ T regulatory cells inhibit cytotoxic activity of CTL and NK cells in humans—impact of immunosenescence, Clinical Immunology, 2006, 119(3), 307-316.
Trzonkowski et al., Ex vivo expansion of CD4(+)CD25(+) T regulatory cells for immunosuppressive therapy, Cytometry A. 2009, 75(3), 175-88.
Trzonkowski et al., First-in-man clinical results of the treatment of patients with graft versus host disease with human ex vivo expanded CD4+CD25+CD 127—T regulatory cells, Clin Immunol. 2009, 133(1), 22-6.
Trzonkowski, All roads lead to T regulatory cells, Transplantation, 2011, 91(2), 150-1.
Maahs et al., 2010, ENd. Metab. Clin. North. Am. vol. 39: 481-497.

* cited by examiner

THERAPEUTIC VACCINE FOR TREATMENT OF DIABETES TYPE 1 IN CHILDREN, APPLICATION OF THE CELL SORTER AND THE METHOD OF MULTIPLYING TREG CELLS TO PRODUCE THERAPEUTIC VACCINE FOR TREATMENT OF DIABETES TYPE 1

CROSS-REFERENCE TO RELATED APPLICATIONS

This application is a divisional of U.S. application Ser. No. 15/852,227, filed Dec. 22, 2017, which is a continuation of U.S. application Ser. No. 14/405,906, filed Dec. 5, 2014, now abandoned, which is a U.S. national phase application filed under 35 U.S.C. § 371 of International Patent Application Number PCT/PL2013/000072, filed Jun. 4, 2013, which claims the benefit of Polish Patent Application Number P.399447, filed Jun. 6, 2012, each of which is incorporated by reference herein in its entirety.

FIELD OF THE INVENTION

The present invention concerns therapeutic vaccine for treatment of diabetes type 1 in children, application of the cell sorter to produce therapeutic vaccine for treatment of diabetes type 1, and the method of multiplying Treg cells in vitro to produce therapeutic vaccine for treatment of diabetes type 1.

PRIOR ART

Diabetes type 1 (DM1A) is a genetically linked disease, however all researchers agree that direct damage to cells in the pancreas is due to autoimmune reaction. Speaking in favour thereof are both the presence of antibodies towards cell antigens, and lymphocytic infiltration to the islets of Langerhans, or the so-called insulitis, accompanied by increased cell apoptosis.

The regulatory T-lymphocytes (Treg) form a specific population in the immune system. Although accounting for less than 1% of the leucocytes in the peripheral blood, they regulate the immune response so that swift elimination of harmful pathogens is possible while our own tissues remain protected. This is because Treg cells do not block other cells of the immune system when foreign pathogens are attacked, but prove strongly inhibiting when the immune system begins to destroy our own tissues and organs. Therefore by analogy, the immunosuppressive action of Treg cells sometimes earns them the name of the “intelligent steroids”.

Reduced numbers of Treg cells in the organism are associated with transplant failures and incidence of allergic and autoimmune diseases. One of the diseases characterised by numerical deficiency of Treg cells, is diabetes type 1 where autoimmune attack destroys the patient’s pancreas.

Known from the international publication WO 2004/110373 is a vaccine composition that comprises modified insulin B chain components suitable for use as immunogenic agents for treatment and prevention of type 1 diabetes.

Known from publication WO 2012/001099, on the other hand, is vaccine containing at least one enterovirus selected from the group including: Coxsackie viruses CAV4, CAV5, CAV6, and echovirus E18, or its component. The description states that the listed enteroviruses are linked to diabetes type 1, which opens new therapeutic and diagnostic possibilities.

Similarly, the description of WO 2012/001100 discloses vaccine comprising e.g. Coxsackie B virus CBV1 to prevent or treat diabetes type 1 It has been found that the virus is strongly associated with the risk of contracting diabetes type 1.

The above publications disclose vaccines intended for treatment of diabetes type 1, nevertheless they are different than the vaccine being the gist of this invention.

In order to increase the effectiveness of treating diabetes type 1 in children it is necessary to search for more effective and successful methods of treating the disease.

GIST OF THE INVENTION

Unexpectedly, it has been found that the new therapeutic vaccine for treatment of diabetes type 1 prevents the disease effectively. Administration of the vaccine according to this invention to patients results in an increase in the primary marker of the pancreas function, i.e. the C-peptide level. In addition, the sorter employed was originally dedicated to cell therapies, which enhances its safety.

The gist of the invention consists in the therapeutic vaccine for treatment of diabetes type 1 in children, which contains:

$$Treg \text{ cells } CD3(+)CD4(+)CD25(\text{high})CD127(-).$$

The gist of this invention further consists in employing the cell sorter to produce the therapeutic vaccine for treatment of diabetes type 1, where the cells are sorted to isolate Treg cells using the algorithm sorting out the following phenotype:

$$CD3(+)CD4(+)CD2S(\text{high})CD127(-)\text{doublet}(-)\text{lineage}(-)\text{dead}(-).$$

The gist of this invention also consists in the method of multiplying Treg cells in vitro to produce therapeutic vaccine for treatment of diabetes type 1, where:

- lymphocytes T CD4+ are isolated by the immunomagnetic method and marked with monoclonal antibodies,
- the sorter-isolated Treg cells are multiplied in the CellGro or X-VIVO medium supplemented with autological inactivated serum and interleukin-2,
- the culture is supplemented with artificial antigen-presenting cells in the 1:1 proportion.

Selected for the marking are the following monoclonal antibodies: anti-CD3, anti-CD4, anti-CDS, anti-CD19, anti-CD14, anti-CD 16, anti-CD25, and anti-CD 127.

The monoclonal antibodies CD3, CD4, CDS, CD19, CD14, CD16, CD25, and CD127 recognise the antigens, and are conjugated with fluorescent dyes.

The antigen-presenting artificial cells are magnetic beads coated with anti-CD3 and anti-CD2S antibodies.

THE FIGURES

FIG. 1—presents the level of Treg cells CD3+CD4+CD2ShighCD127-FoxP3+ in children suffering from diabetes type 1, subject to the Treg cell therapy (n=10) over four months’ observation. The value at point “−10 days” represents the day the blood was drawn for Treg cell isolation. The grey columns present the results obtained for children not administered the Treg lymphocyte infusion (control group; n=10). The values are given at their median, minimum, and the maximum levels. The statistically significant values ($p<0.05$) are marked with "*".

Figure 2:
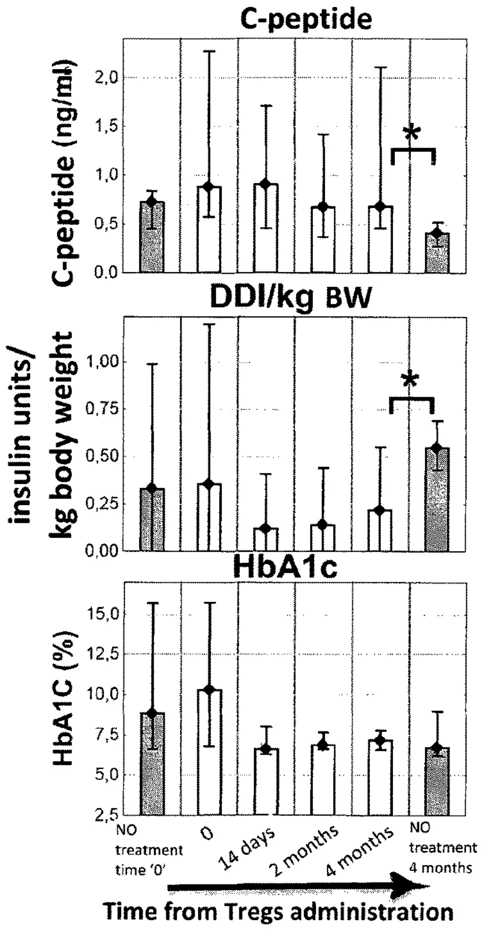

FIG. 2—presents the C-peptide, the daily insulin dose/kg BW(DDI/kg), and the HbA1C in the tested children with diabetes type 1, subject to the Treg cells therapy (n=10) over the four months' observation. The results for the patients not administered the cell preparation (control group; n=10) are presented in grey columns. The values are given at their median, minimum, and the maximum levels, and the statistically significant values ($p<0.05$) are marked with "*".

The invention is illustrated with the following embodiment, which is exemplary, i.e. not limiting in nature.

EXEMPLARY EMBODIMENT 250 ml of peripheral blood was sampled from each patient with the assistance from an anaesthesiologist. In the case of children whose body weight was less than 50 kg the sampled blood volume accounted for 0.5% of the body weight (BW). This concerns patients under the age of 18.

The collected blood was processed at the Regional Centre of Blood Donation and Treatment in Gdansk to extract the huffy coat and serum. Isolated from the buffy coat were peripheral blood mononuclear cells (PBMC) through centrifuging in the Ficoll/Uropolin concentration gradient. Lymphocytes T CD4+ were then separated by the immunomagnetic method (separation purity: 96-99%) using the CD4+ T enrichment kit and marked with the following monoclonal antibodies (mAb): anti-CD3, anti-CD4, anti-CDS, anti-CD19, anti-CD14, anti-CD16, anti-CD25, and anti-CD127 (Sul mAb/$10^6$ cells). Among the listed antibodies those which recognize antigens CD14, CD16, CD19, and CDS were conjugated with the same dye. The purpose of that dying scheme was to exclude the cells positive with respect to the listed antigens (i.e. monocytes, NK cells, lymphocytes Band cytotoxic T lymphocytes) without the need to introduce additional fluorochromes, which reduces the undesirable phenomenon of fluorescent spectra overlapping. Then, the cells were sorted to separate Tregs using a sorting cytometer to the algorithm sorting the following phenotype:

$$CD3(+)CD4(+)CD2S(\text{high})CD127(-)\text{doublet}(-)\text{lineage}(-)\text{dead}(-).$$

The adopted exemplary dying scheme (antibody; dye name acronym, full name of the dye)

- antiCD127 FITC (Fluorescein isothiocyanate)
- antiCD25 PE (phycoerythrin)
- antiCD16 PerCP (Peridinin Chlorophyll Protein Complex)
- antiCD19 PerCP (Peridinin Chlorophyll Protein Complex)
- antiCD8 PerCP (Peridinin Chlorophyll Protein Complex)
- antiCD14 PerCP (Peridinin Chlorophyll Protein Complex)
- antiCD4 APC (allophycocyanin)
- antiCD3 Pacific Blue/Pacific Blue or equivalents evoked to emit fluorescent light in similar spectrum ranges.

The purity of the thus isolated Treg cells was ~100% [median(min-max): 98% (97-99)]. An important modification compared to our earlier procedure consisted in applying the Influx cell sorter designed in accordance with the good manufacturing practices (GMP). The sorter is fitted with a replaceable sample flow line, which eliminates the risk of sample cross-contamination among the patients. Moreover, applied was the CellGro medium meeting the GMP standards or X-VIVO. The medium was supplemented with autological inactivated serum (10%) and interleukin-2 (1000 U/ml). Introduced into the culture were the so-called antigen-presenting artificial cells [magnetic beads coated with anti-CD3 and anti-CD28 antibodies in the 1:1 proportion. The cells were cultivated until the appropriate number was attained, though no longer than for 2 weeks [median(min-max): 10 days (7-12)].

The above indicated modifications allowed the attainment of substantially improved stability and quality of the cultured Treg cells in the final product. The actual application of the preparation in therapy was conditional on satisfaction of the following criteria: factor FoxP3 expression above 90% [median(min-max)=93%(90-97)], positive result of the IFNy production inhibition test, and negative results of microbiological tests—no genetic material of the HBV, HCV, or HIV viruses, and no bacterial contamination in the culture supernatants. Before infusion, the cells were washed with PBS, the magnetic beads removed, and administered in slow intravenous injection in 250 ml 0.9% NaCl under supervision of the anaesthesiologist within 1 h after the product release. The therapeutic dose was $20\times10^6$/kg BW (n=6), or $10\times10^6$/kg BW (n=4; whenever no higher number of cells had been achieved upon cultivation for 2 weeks), or $30\times10^6$/kg body weight. The control group was made up of patients who met all above-listed criteria of inclusion in the test, except for appropriate venous access, hence were not treated with the Treg vaccine. The test was not randomised, nor was there a blank sample introduced, and the children of the control group were not subject to any medical intervention related to the pending tests (blood sampling, simulated transfusion, or the like). Table 1 provides the characteristics of the tested groups. The test endpoints were as follows: the fasting C-peptide level, the HbA1c concentration, the insulin requirement, especially the daily dose (DDI)=0.SUI/kg BW adopted as the remission indicator. The test was conducted in accordance with the procedure approved by the Independent Research Bioethics Committee at the Medical University of Gdansk (NKEBN/8/2010). A written consent to the above procedure was obtained from each patient and the parents.

None of the patients was observed to develop any serious infections, episodes of acute hyper-/hypoglycaemia, or any other undesirable side effects of the Tregs vaccine at any time over the test period. In case of one patient the Treg cell infusion date coincided with flu diagnosed a day after the Treg cells had been administered.

Beginning on the infusion date and continuously afterwards the recorded Treg lymphocyte percent level in the peripheral blood was significantly increased (Wilcoxon test, p=0.04) (FIG. 1).

Two weeks after the Treg cell infusion all patients subject to the therapy were observed to demonstrate substantially reduced demand for exogenous insulin and a reduced HbA1c level (FIG. 2).

The first significant differences between the test group and the patients of the control group were observed six months after formulation of the diabetes diagnosis (5-6 months after the Treg cell infusion). The treated patients continued in the remission phase [DDI median(min-max)=0.24 UI/kg BW (0-0.55)], whereas the control group experienced the end of remission [DDI median(min-max)=0.55 UI/kg BW (0.43-0.69)] (Mann-Whitney U test, p=0.03). In addition, the children treated with Treg cells proved to have a significantly higher level of C-peptide [median(min-max): 0.65 ng/ml (0.46-2.11) vs. 0.40 ng/ml (0.15-0.54)] (Mann-Whitney U test, p=0.04) (FIG. 3). No differences with respect to therapy effectiveness were observed in the patients who had been administered Treg cells dosed at 20×10$^6$/kg BW or 10×10$^6$/kg BW. Therefore, all results of the test group are presented en block.

LITERATURE

1. Marek N, Krzystyniak A, Ergenc I, Cachet O, Misawa R, Wang L J, Golqb K, Wang X, Kilimnik G, Hara M, Kizilel S, Trzonkowski P, Millis J M, Witkowski P. Coating human pancreatic islets with CD4(+)CO25(high)CD127(−) regulatory T cells as a novel approach for the local immunoprotection. Ann Surg. 2011; 254(3):512-8; discussion 518-9.
2. Marek N, Bieniaszewska M, Krzystyniak A, Juscinska J, Mysliwska J, Witkowski P, Hellmann A, Trzonkowski P. The time is crucial for ex vivo expansion of T regulatory cells for therapy. Cell Transplant. 2011 (20):1747-1758;
3. Trzonkowski P. All roads lead to T regulatory cells. Transplantation. 2011; 91(2):150-1.
4. Trzonkowski P, Bieniaszewska M, Juscinska J, Dobyszuk A, Krzystyniak A, Marek N, Mysliwska J, Hellmann A First-in-man clinical results of the treatment of patients with graft versus host disease with human ex vivo expanded CD4+CD25+CD127− T regulatory cells. Clin Immunol. 2009; 133(1):22-6.
5. Trzonkowski P, Szarynska M, Mysliwska J, Mysliwski A Ex vivo expansion of CD4(+)CD25(+) T regulatory cells for immunosuppressive therapy. Cytometry A 2009; 75(3):175-88.

6 Ryba M, Marek N, Hak t, Rybarczyk-Kapturska K, Mysliwiec M, Trzonkowski P, Mysliwska J. Anti-TNF rescue CD4+Foxp3+ regulatory T cells in patients with type 1 diabetes from effects mediated by TNF. Cytokine. 2011; 55(3):353-61.

7. Trzonkowski P, Szmit E, Mysliwska J, Mysliwski A CD4+CD25+ T regulatory cells inhibit cytotoxic activity of CTL and NK cells in humans-impact of immunosenescence. Clin Immunol. 2006; 119(3):307-16.
8. & Trzonkowski P, Szmit E, Mysliwska J, Dobyszuk A, Mysliwski A CD4+CD25+ T regulatory cells inhibit cytotoxic activity of T CDS+ and NK lymphocytes in the direct cell-to-cell interaction. Clin Immunol. 2004; 112 (3):258-67.
9. Trzonkowski P, Zaucha J M, Mysliwska J, Balon J, Szmit E, Halaburda K, Bieniaszewska M, Mlotkowska M, Hellmann A, Mysliwski A Differences in kinetics of donor lymphoid cells in response to G-CSF administration may affect the incidence and severity of acute GvHD in respective HLA-identical sibling recipients. Med Oncol. 2004; 21(1):81-94.
10. Golqb K, KrzystyniakA, Marek-Trzonkowska N, Misawa R, Wang L J, Wang X, Cochet O, Tibudan M, Langa P, Millis J M, Trzonkowski P., Witkowski P. Impact of culture medium on CD4+ CD25highCD127lo/neg Treg expansion for the purpose of clinical application. Int Immunopharmacol. 2013. doi:pii: S1567-5769(13)00058-1. 10.1016/j.intimp.2013.02.016

TABLE 1

CLINICAL CHARACTERISTICS OF THE PATIENTS

| | Treg treated (n = 10) | Untreated control group (n = 10) |
|---|---|---|
| Age (years) [median; min-max] | 12.2; 8-16 | 11.8; 7-16 |
| BMI [median; min-max] | 16,9; 14.2-21.5 | 16.9; 14.2-20.7 |
| Glycaemia on empty stomach at diagnosis (mg %) median; min-max] | 354; 151-588 | 354; 151-598 |
| Polydipsia at diagnosis (number of patients) | 5 | 8 |
| Polyuria at diagnosis (number of patients) | 5 | 8 |
| Body weight loss at diagnosis (number of patients) | 4 | 3 |
| Capillary blood pH at diagnosis [median; min-max] | 7.39; 7.36-7.46 | 7.39; 7.34-7.53 |
| Capillary blood $pO_2$ at diagnosis (mmHg) [median; min-max] | 69.3; 63.4-88.0 | 69.0; 56.9-86.2 |
| Capillary blood $pCO_2$ at diagnosis (mmHg) [median; min-max] | 39.1; 28.0-41.8 | 38.0; 24.0-41.0 |
| $HCO_3$ at diagnosis (capillary blood-mmHg) [median; min-max] | 23.85; 18.8-25.0 | 23.3; 21.3-25.2 |
| Acid base balance (BE-mEq/l) [median; min-max] | −0.55; −7.8-1.0 | −0.6; −7.0-0.9 |
| Capillary blood Sat02 at diagnosis (%) [median; min-max] | 94.1; 90.2-97.3 | 95.5; 92.4-98.0 |
| Ig anti-GAD65 (number of patients) | 10 | 10 |
| Ig anti-ICA (number of patients) | 5 | 5 |
| Ig anti-IAA (number of patients) | 9 | 8 |

The invention claimed is:

1. A method of expanding a population of CD3(+)CD4(+)CD25(high)CD127(−) Treg cells comprising:

providing CD3(+)CD4(+)CD25(high)CD127(−) Treg cells from a child with type 1 diabetes, and propagating the CD3(+)CD4(+)CD25(high)CD127(−) Treg cells ex vivo in medium supplemented with interleukin-2 and autologous inactivated serum in the presence of magnetic beads coated by anti-CD3 and anti-CD28 antibodies for 7-14 days to produce an expanded population of CD3(+)CD4(+)CD25(high)CD127(−) Treg cells;

wherein more than 90% of the expanded population of Treg cells express factor FoxP3, and wherein administration of the expanded population of Treg cells to the child in an amount between 10×10$^6$ cells/kg body weight and 30×10$^6$ cells/kg body weight results in an increase in the C-peptide level in the child at 5 months after the administration, further comprising administering the expanded population of Treg cells to the child in an amount between 10×10$^6$ cells/kg body weight and 30×10$^6$ cells/kg body weight.

2. The method of claim 1, wherein the CD3(+)CD4(+)CD25(high)CD127(−) Treg cells are isolated by labeling isolated T lymphocyte cells with monoclonal antibodies and sorting the T lymphocyte cells using a sorting device.

3. The method of claim 2, wherein the sorted cells comprise a Treg cell population having a purity of at least 97%.

4. The method of claim 1, comprising propagating the CD3(+)CD4(+)CD25(high)CD127(−) Treg cells ex vivo with 1000 U/ml interleukin-2 and 10% autologous inactivated serum.

* * * * *